United States Patent
Jin et al.

(10) Patent No.: US 12,194,038 B2
(45) Date of Patent: Jan. 14, 2025

(54) USE OF FLIBANSERIN IN PREPARATION OF DRUG FOR TREATING ANDROGENIC ALOPECIA

(71) Applicant: SHANGHAI DIMAIHE BIOTECHNOLOGY CO., LTD., Shanghai (CN)

(72) Inventors: Liang Jin, Nanjing (CN); Yingjie Sun, Nanjing (CN)

(73) Assignee: SHANGHAI DIMAIHE BIOTECHNOLOGY CO., LTD., Shanhai (CN)

( * ) Notice: Subject to any disclaimer, the term of this patent is extended or adjusted under 35 U.S.C. 154(b) by 0 days.

(21) Appl. No.: 18/718,086

(22) PCT Filed: Jan. 23, 2024

(86) PCT No.: PCT/CN2024/073632
§ 371 (c)(1),
(2) Date: Jun. 10, 2024

(87) PCT Pub. No.: WO2024/104511
PCT Pub. Date: May 23, 2024

(65) Prior Publication Data
US 2024/0415831 A1    Dec. 19, 2024

(30) Foreign Application Priority Data
Dec. 5, 2022 (CN) ............. 202211546154

(51) Int. Cl.
*A61K 31/496* (2006.01)
*A61P 17/14* (2006.01)

(52) U.S. Cl.
CPC ............ *A61K 31/496* (2013.01); *A61P 17/14* (2018.01)

(58) Field of Classification Search
CPC .................................................. A61K 31/496
See application file for complete search history.

(56) References Cited

U.S. PATENT DOCUMENTS

| 2003/0175817 A1 | 9/2003 | Ikeda et al. |
| 2004/0014732 A1 | 1/2004 | Sovak et al. |

FOREIGN PATENT DOCUMENTS

| CN | 1416416 A | 5/2003 |
| CN | 1551879 A | 12/2004 |
| CN | 101304746 A | 11/2008 |
| CN | 114159440 A | 3/2022 |

OTHER PUBLICATIONS

Chen et al. "Drug for Treating Female Sexual Dysfunction—Flibanserin" Herald of Medicine, vol. 35, No. 4, Apr. 30, 2016, English Translation, 3 pages.
Chen et al., "Research Progress on the Relationship Between Androgen Receptors and Androgenic Alopecia" Southern China Journal of Dermato-Venereology, vol. 8, No. 4, Dec. 31, 2001, 3 pages, English Translation.
Clayton et al. "Flibanserin: a potential treatment for Hypoactive Secual Desire Disorder in premenopausal women" Drug Evaluation, vol. 6, No. 5, Dec. 31, 2010, 15 pages.
CNIPA, Search Report, Application No. PCT/CN2024/073632, mailed Mar. 28, 2024, 6 pages.
CNIPA, Written Opinion of the International Searching Authority, Application No. PCT/CN2024/073632, mailed Mar. 28, 2024, 4 pages, English Translation, 4 pages.
Wang et al., "The Mechanism and Drug Treatment Progress of Androgenic Alopecia" Journal of Clinical Medical Literature, vol. 5, No. 33, Dec. 31, 2018, 3 pages. English Translation, 3 pages.

*Primary Examiner* — Yong S. Chong
(74) *Attorney, Agent, or Firm* — Ziegler IP Law Group LLC

(57) ABSTRACT

The present invention discloses the use of flibanserin in the preparation of a drug for treating androgenic alopecia. The results of cell models show that flibanserin at a low concentration can inhibit the proliferation of Lncap cells, showing a pharmacodynamic activity at the cellular level. The results of animal experiments show that flibanserin can reverse androgen-mediated androgenic alopecia damage, treat androgenic alopecia and restore hair growth. Therefore, flibanserin can be used in the preparation of a drug for treating androgenic alopecia.

4 Claims, 5 Drawing Sheets

DP nuclear protein and cytoplasmic protein
separation experiment-AR

USE OF FLIBANSERIN IN PREPARATION OF DRUG FOR TREATING ANDROGENIC ALOPECIA

TECHNICAL FIELD

The present invention belongs to the field of small molecule drugs, and relates to the use of flibanserin in the preparation of a drug for treating androgenic alopecia.

BACKGROUND ART

Androgenic alopecia (AGA), a disease characterized by a progressive decrease in hair density, usually starting with recession of the frontal hairline and proceeding with progressive thinning and loss of the hair on the vertex of the scalp, is an autosomal dominant disorder. Both women and men have higher levels of androgen receptor and type I and type II 5a-reductase activity in frontal hair follicles than in occipital hair follicles. The type I and type II a-reductase activity in frontal hair follicles in men is three times the activity in frontal hair follicles in women. Therefore, male androgenic alopecia is considered to be an androgen-dependent disease, with an overall prevalence of 21.3% in Chinese male, with an increase in incidence with age. AGA seriously affects patients socially and psychologically, and the patients are eager to seek treatment. Pathological features of AGA include hair follicle miniaturization, shortened hair follicle anagen and prolonged telogen. AGA is clinically manifested as vellus hairs replacing terminal hairs (vellus hairs being defined as <30 μm in diameter and <30 μm in length; transitional hair width between 30 and 40 μm; terminal hair >40 μm) and a decrease in total hair density (hairs per square centimeter) as the main clinical features. Replacement of terminal follicles with vellus follicles, macrophage infiltration in perifollicular area, increased sebaceous gland size and thinning of the dermis can also be seen histologically. The cycle of hair follicle growth is divided into four phases: anagen when hair matrix keratinocytes located around dermal papilla cells (DPCs) proliferate and hair shafts grow; catagen when hair follicles undergo tightly controlled apoptosis and extracellular matrix remodeling; telogen when hair shafts are attached to the bulb base of hair follicles and can be shed by grooming; and exogen when hairs of telogen are shed. Testosterone (T) is one of the major sex hormones in the human body, and 5a-reductase (5GR) expressed in DPCs catalyzes the conversion of T to the more active 5a-dihydrotestosterone (DHT). DHT binds to the androgen receptor (AR) on hair matrix cells to form a DHT-AR complex that enters the nucleus and that acts as a transcription factor to induce hair follicle dermal papilla cells to secrete a variety of cytokines, such as transforming growth factor-B (TGF-B), interleukin-la (IL-la) and tumor necrosis factor-a (TNF-a), which can induce premature termination of the hair follicle anagen, leading to AGA. Androgenic alopecia is the result of an abnormal sensitivity of scalp hair follicles to circulating androgens. Under the induction of androgens, the expression of the androgen receptor increases, thereby altering the mesenchymal-epithelial interactions in the hair follicles, which affects the hair growth, the dermal papilla size, the dermal papilla cells and the activity of keratinocytes and melanocytes. The Wnt signaling pathway regulates the dermal papilla cells and may play a key role in the effects of androgens on hair growth. However, the underlying molecular mechanisms of androgen-related actions remain largely unknown.

Up to now, there are only two FDA-approved drugs for the treatment of androgenic alopecia, oral finasteride and topical minoxidil. Finasteride is a 5a-reductase inhibitor and treats alopecia by reducing the level of DHT in the body. Minoxidil is a vasodilator and can be used for treating alopecia by improving hair follicle microcirculation. Other treatments include non-drug treatments such as laser therapy, hair transplantation, and stem cell therapy. However, these treatments have significant side effects such as sexual dysfunction and hirsutism, and have problems such as high cost. Therefore, it is of great significance to find a new drug for treating androgenic alopecia with less side effects.

SUMMARY OF THE INVENTION

In view of the above defects in the prior art, an objective of the present invention is to provide the use of flibanserin in the preparation of a drug for treating androgenic alopecia.

The objective of the present invention can be achieved by the following technical solutions:

Provide is the use of flibanserin in the preparation of a drug for treating androgenic alopecia.

As a preferred aspect of the present invention, flibanserin can increase hair length, the ratio of anagen to telogen, the ratio of epidermal thickness to dermal thickness, the number of hair follicles per unit area, and the diameter of hair follicles.

As a preferred aspect of the present invention, provided is the use of flibanserin in the preparation of a drug for reversing androgen-mediated androgenic alopecia damage, treating androgenic alopecia, and restoring hair growth.

Provided is the use of flibanserin in the preparation of a drug for inhibiting an androgen receptor dimer and preventing it from entering the nucleus.

Provided is the use of an androgen receptor dimer as a therapeutic target in screening a drug for treating androgenic alopecia. Flibanserin is a compound for treating androgenic alopecia, which is screened using a computer simulation technology in view of the structure of the androgen receptor dimer.

Beneficial Effects:

In the present invention, an inhibitor of the androgen receptor dimer is screened by combining a computer simulation technology with in vivo and in vitro drug screening assays. On the one hand, the compound structurally has a binding activity to the structure of the androgen receptor dimer, with clear action target and strong specificity relative to minoxidil, and on the other hand, the compound is an inhibitor of the androgen receptor dimer, wherein the binding of the compound to the androgen receptor dimer can inhibit the nuclear localization of the androgen receptor dimer, and inhibit the recruitment of downstream activators of the complex and the binding to androgen receptor reaction elements, thereby blocking the downstream gene response and treating androgenic alopecia. Compared with finasteride, the drug has a mild action condition, and does not cause downstream reactions mediated by the androgen receptor at other sites, thereby greatly reducing the side effects of the drug for treating androgenic alopecia.

The results of cell models show that flibanserin at a low concentration can inhibit the proliferation of Lncap cells, showing a pharmacodynamic activity at the cellular level. The results of animal experiments show that in the flibanserin administration group and finasteride administration group, the hairs of mice restore to varying degrees compared with the model group, and the hair growth is similar to that in the control group and the complete blank group. The effective rate of animal hair restoration is 85.7% in the flibanserin group and 71.4% in the finasteride group. Compared with the model group, HE staining of tissue sections shows an increase in hair length, an increase in the ratio of anagen to telogen, an increase in the ratio of epidermal thickness to dermal thickness, an increase in the number of hair follicles per unit area, and an increase in the diameter of hair follicle in the flibanserin group. Therefore, the results shows that flibanserin can reverse androgen-mediated androgenic alopecia damage, treat androgenic alopecia and restore hair growth.

DETAILED DESCRIPTION OF EMBODIMENTS

Example 1

Reagents and cells involved in cell-related experiments: dihydrotestosterone, Batch No. CHB16A802100G. DMSO, Batch No. #RNBK5094. Flibanserin, Batch No. W1608Z45834. 5 mg of flibanserin was dissolved in 1.28 mL of DMSO to prepare a mother liquor with a concentration of 10000 uM. The Lncap cell line was a human prostate cancer cell line, which was purchased from Xiamen Immocell Biotechnology Co., Ltd., sample number: 20210106-06, biosafety level: BSL-1, epithelioid, adherent growth; single cells and loosely adherent cell clusters. The culture conditions are as follows: RPMI Medium 1640 (Invitrogen, 11875093) 88 ml+FBS (Gibco) 10 ml+Glutamax (Invitrogen, 35050) 1 ml+Sodium Pyruvate 100 mM Solution (Invitrogen, 11360070) 1 ml. The cells are responsive to dihydrotestosterone (involved in growth regulation and acid phosphatase ACP production).

Dihydrotestosterone was dissolved in DMSO to prepare a mother liquor at 0.01 mol/L, which was sequentially diluted to gradient concentrations of $10^{-5}$ M, $10^{-6}$ M, $10^{-7}$ M, $10^{-8}$ M, $10^{-9}$ M, and $10^{-10}$ M with a medium; the diluted dihydrotestosterone was added into adherent Lncap cells; the cells were cultured for 48 h, 72 h and 96 h; the proliferation of the Lncap cells was determined by MTT; in combination with RT-PCR, the response of downstream genes KLK3 and KLK2 was explored at different concentrations; and the concentration of the dihydrotestosterone ($10^{-9}$ M) at which the proliferative effect was most pronounced and the response of the downstream genes was most pronounced was used as the optimal androgen modeling concentration for the Lncap cells. The drugs at gradient concentrations of $10^{-3}$ uM, $10^{-1}$ uM, 1 uM, 10 uM, 50 uM and 100 uM were added into the Lncap cells after androgen modeling for co-culture for 24 h, 48 h and 96 h, respectively, and the inhibition rate of flibanserin on the proliferation of the Lncap cells was determined by MTT. The results show that flibanserin at a low concentration can inhibit the proliferation of Lncap cells, showing a pharmacodynamic activity at the cellular level.

Figure 1:
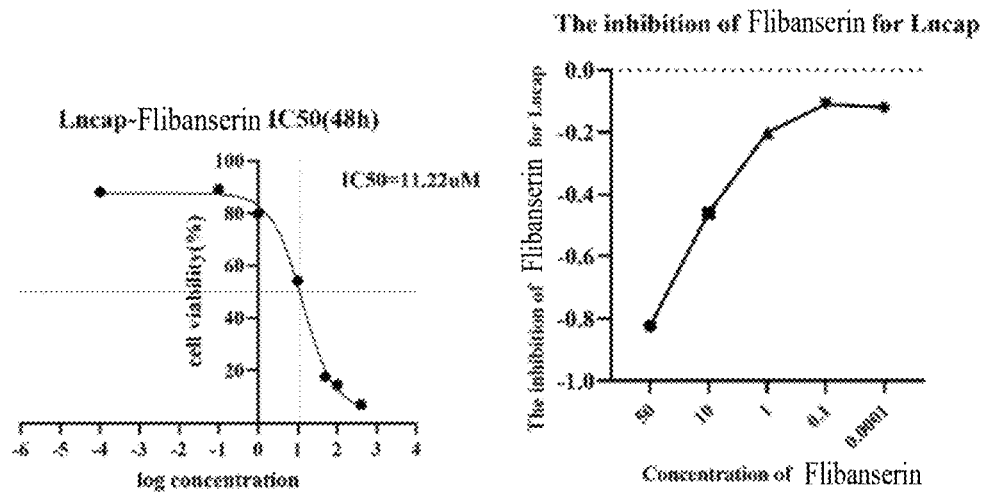
FIG. 1: Inhibition of proliferation of prostate cancer cells Lncap stimulated by dihydrotestosterone.

The experimental results were processed by Excel software, and the experimental results are as shown in FIG. 1 and the table below:

TABLE 1

Promotion of proliferation of Lncap cells for 48 h by different concentrations of DHT

| DHT concentration | OD value in DHT group-OD value in control group | | | | | Mean proliferation rate |
|---|---|---|---|---|---|---|
| $10^{-5}$ uM | −0.35623 | −0.27116 | −0.08071 | 0.052151 | 0.010499 | −12.91% |
| $10^{-6}$ uM | 0.061983 | −0.0322 | 0.26443 | 0.002439 | 0.019578 | 6.30% |
| $10^{-7}$ uM | −0.09862 | 0.025021 | 0.035831 | 0.090217 | 0.26348 | 7.77% |
| $10^{-8}$ uM | −0.08997 | 0.040342 | 0.087079 | 0.098522 | 0.247512 | 9.47% |
| $10^{-9}$ uM | −0.01084 | 0.001247 | 0.051255 | 0.003247 | 0.356129 | 10.01% |
| $10^{-10}$ uM | 0.223767 | −0.08268 | 0.03327 | −0.02634 | −0.02935 | 2.79% |

The experimental results show that it varies in terms of the promotion of the proliferation of the Lncap cells by different concentrations of DHT, with the most significant promotion of the proliferation of the Lncap cells with $10^{-9}$ uM DHT. This concentration is therefore selected as the optimal concentration for drug modeling.

TABLE 2

Inhibition of proliferation of Lncap cells for 48 h by different concentrations of flibanserin

| Flibanserin concentration | OD value in administration group-OD value in control group | | | | | Mean proliferation inhibition rate |
|---|---|---|---|---|---|---|
| 100 uM | 0.134472 | 0.115686 | 0.119048 | 0.175074 | 0.18125 | 85.49% |
| 50 uM | 0.17381 | 0.142398 | 0.155602 | 0.188564 | 0.221751 | 82.36% |
| 10 uM | 0.359202 | 0.607639 | 0.556242 | 0.530151 | 0.653846 | 45.86% |

TABLE 2-continued

Inhibition of proliferation of Lncap cells for
48 h by different concentrations of flibanserin

| Flibanserin concentration | OD value in administration group-OD value in control group | | | | | Mean proliferation inhibition rate |
|---|---|---|---|---|---|---|
| 1 uM | 0.794667 | 0.816351 | 0.701994 | 0.834492 | 0.847167 | 20.11% |
| 0.1 uM | 0.782097 | 0.915294 | 0.920354 | 0.83995 | 0.993837 | 10.97% |
| 0.001 uM | 0.720039 | 0.980975 | 0.894256 | 0.840532 | 0.968112 | 11.92% |

The experimental results show that the inhibition on the proliferation of Lncap cells by adding different concentrations of flibanserin after modeling with $10^{-9}$ M DHT is increased with the increase of the concentration of flibanserin, and therefore flibanserin has a pharmacodynamic activity at the cellular level.

Example 2

Animal experiment-related reagents: testosterone propionate, Batch No. T818615. Soybean oil, Batch No. A23GS146219. 80 mg of testosterone propionate was dissolved in 40 mL of soybean oil to prepare a solution at 2 mg/mL. Finasteride, Batch No. A16GS145548. 0.28 mg of finasteride was dissolved in 20 mL of physiological saline to prepare a solution at $1.4 \times 10^{-2}$ mg/mL. Flibanserin, Batch No. W1608745834, 0.32 mg of flibanserin was dissolved in 20 mL of physiological saline to prepare a solution at $1.6 \times 10^{-2}$ mg/mL The experimental animals are male C58BL/6 mice, non-inbred closed colony, weighing 18-22 g, aged 5 weeks, certificate number: No. 202207119, provided by the Institute of Comparative Medicine, Yangzhou University. In the laboratory, room temperature is 20° C.-22° C., the relative humidity is 40%-60%, ventilation is provided by a ventilation fan, and the natural light source is provided for 12 h/day. The mice were caged, with 7 mice per cage, and the cages were cleaned every three days.

Before the injection of testosterone propionate for modeling, pre-treatment was first performed, wherein the pre-treatment comprises: fixing the mice, shaving off the hairs on the back of the mice by an electric shaver, and unhairing vellus hairs using an unhairing cream. The mice were grouped into a complete blank group (no treatment except unhairing), a control group (injection of soybean oil 0.2 mL+intragastric administration of physiological saline 0.1 mL), a model group (injection of testosterone propionate solution 0.2 mL+intragastric administration of physiological saline 0.1 mL), a model group+finasteride (injection of testosterone propionate solution 0.2 mL+intragastric administration of finasteride solution 0.1 mL), and a model group+ flibanserin (injection of testosterone propionate solution 0.2 mL+intragastric administration of flibanserin solution 0.1 mL), with 7 mice/cage, wherein before the intragastric administration, the testosterone propionate solution was injected for modeling for 21 days, and the success rate of the modeling was judged by observing the growth of hairs on the back of the mice. After successful modeling, the intragastric administration was performed for 4 weeks on the basis of the injection of the testosterone propionate solution. After the administration was completed, the effective rate (percentage of hair restoring mice to the total number of mice) of the drug was subjected to statistical analysis, and the ratio of the area of the hair growing part to the area of the unhairing part in mice was subjected to statistical analysis. The mouse hairs were taken from multiple points at different hair restoring parts on the back of the mice for length measurement and statistical analysis. The mice were sacrificed by cervical dislocation, and the back skin was taken, wherein a part of the back skin was frozen at −80° C. for extracting protein and performing a nuclear protein and cytoplasmic protein separation experiment to explore the inhibition of the drug on the nuclear localization of the androgen receptor dimer, and a part of the back skin was fixed with 4% paraformaldehyde (Cat. No.: AF030) for 48 h, and then subjected to tissue section and HE staining. The number of hair follicles, the diameter of dermal papilla, and the ratio of hair follicle anagen to telogen per unit area of the back skin of the mice were counted under microscope, and the efficacy of flibanserin was subjected to statistical analysis by comparing with the model group, the complete blank group, the control group and the positive drug finasteride group. Determination criteria: The unhairing area of the back of the mice after unhairing was measured, noted as A, the hair growing area of the back of the mice after the completion of the administration was measured, noted as B, and the mean value of the A/B values in each group was taken as the effective rate of animal hair restoration.

Figure 2:
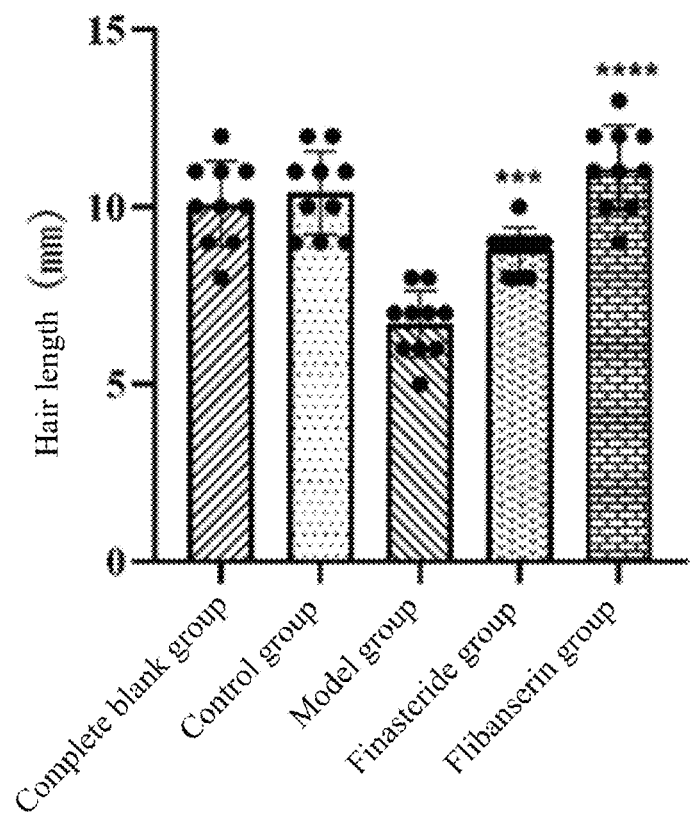
FIG. 2: Statistical diagram of hair length in AGA model mice treated with flibanserin.
Figure 3:
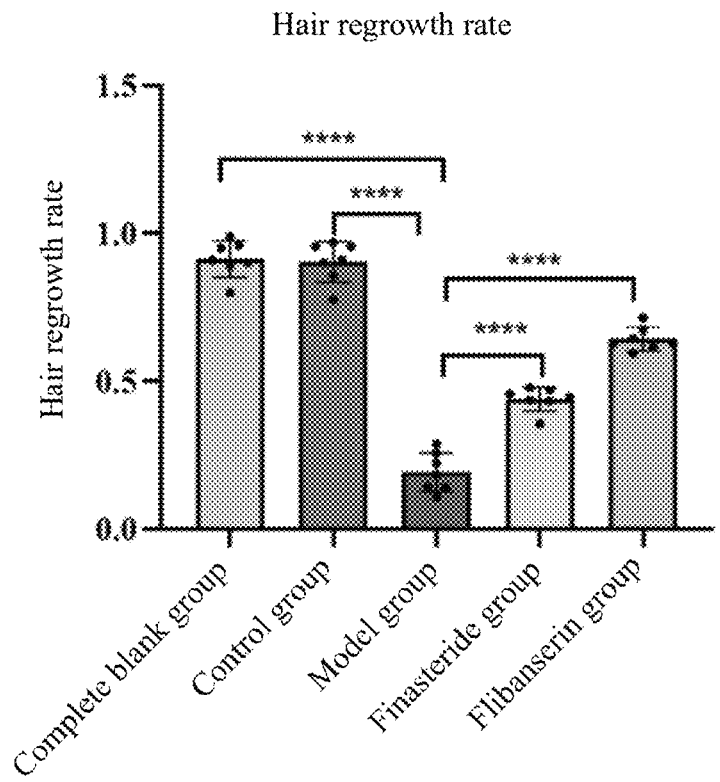
FIG. 3: Histogram of hair regrowth rate in AGA model mice treated with flibanserin.
Figure 4:
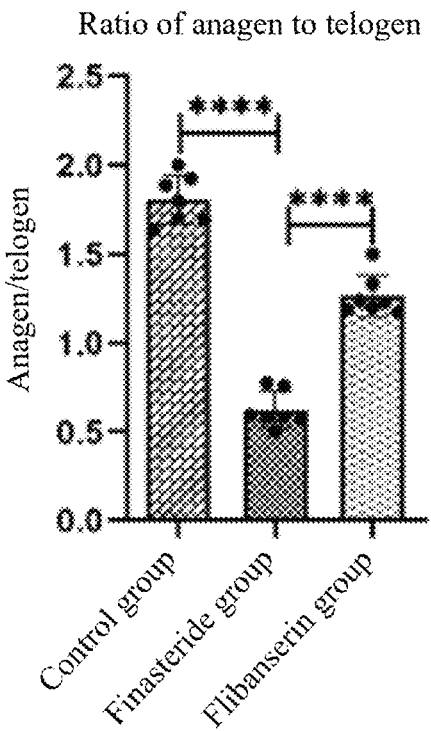
FIG. 4: Histogram of the ratio of hair follicle anagen to telogen in AGA model mice treated with flibanserin.
Figure 5:
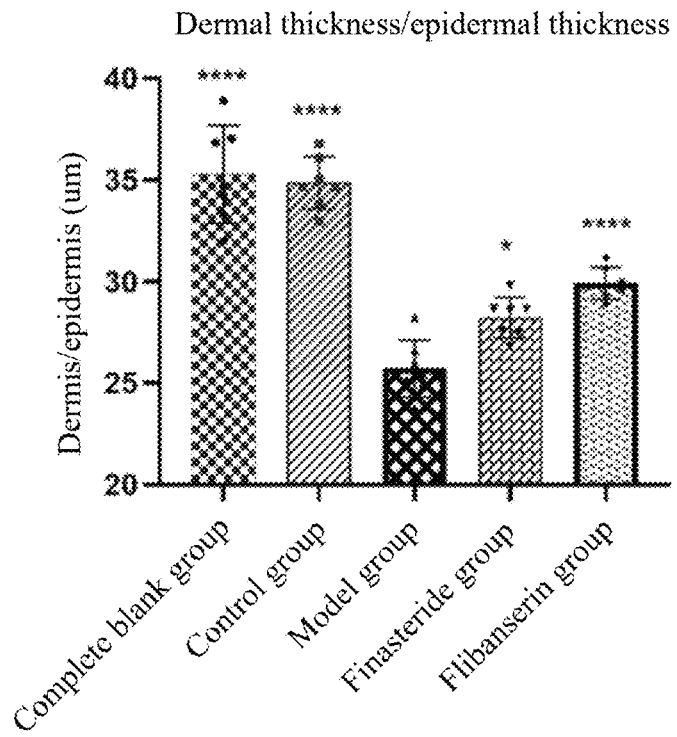
FIG. 5: Histogram of the ratio of dermal thickness to epidermal thickness in AGA model mice treated with flibanserin.
Figure 6:
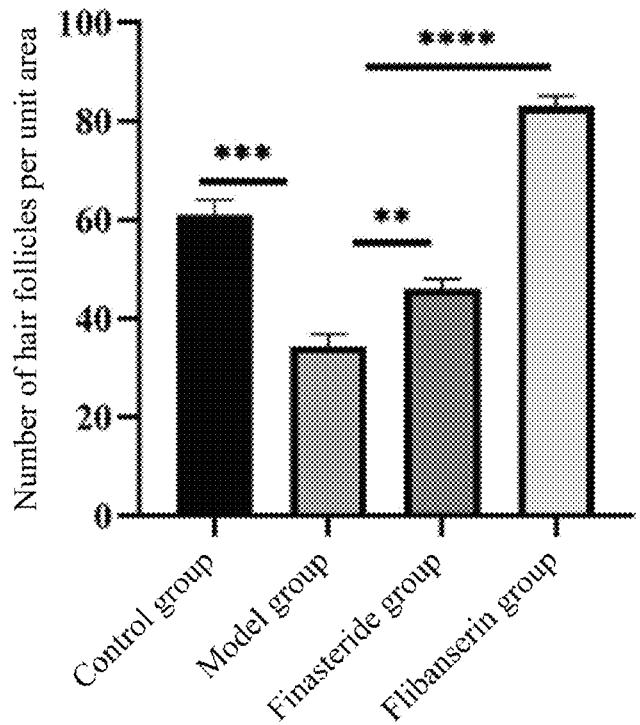
FIG. 6: Statistical histogram of the number of hair follicles per unit area in AGA model mice treated with flibanserin.
Figure 7:
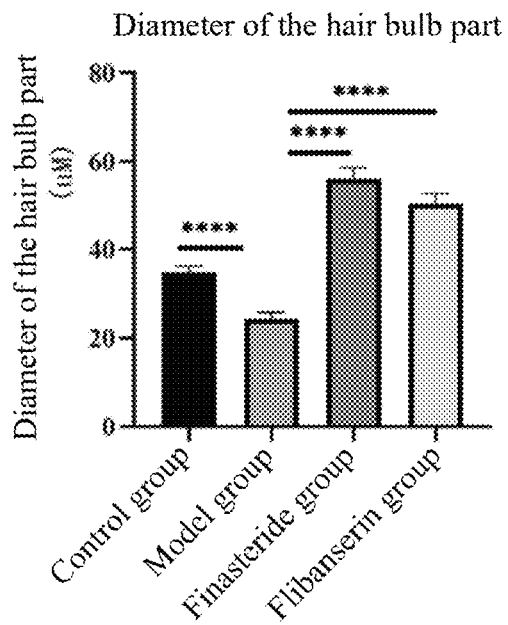
FIG. 7: Statistical histogram of the diameter of hair follicles in AGA model mice treated with flibanserin.
Figure 8:
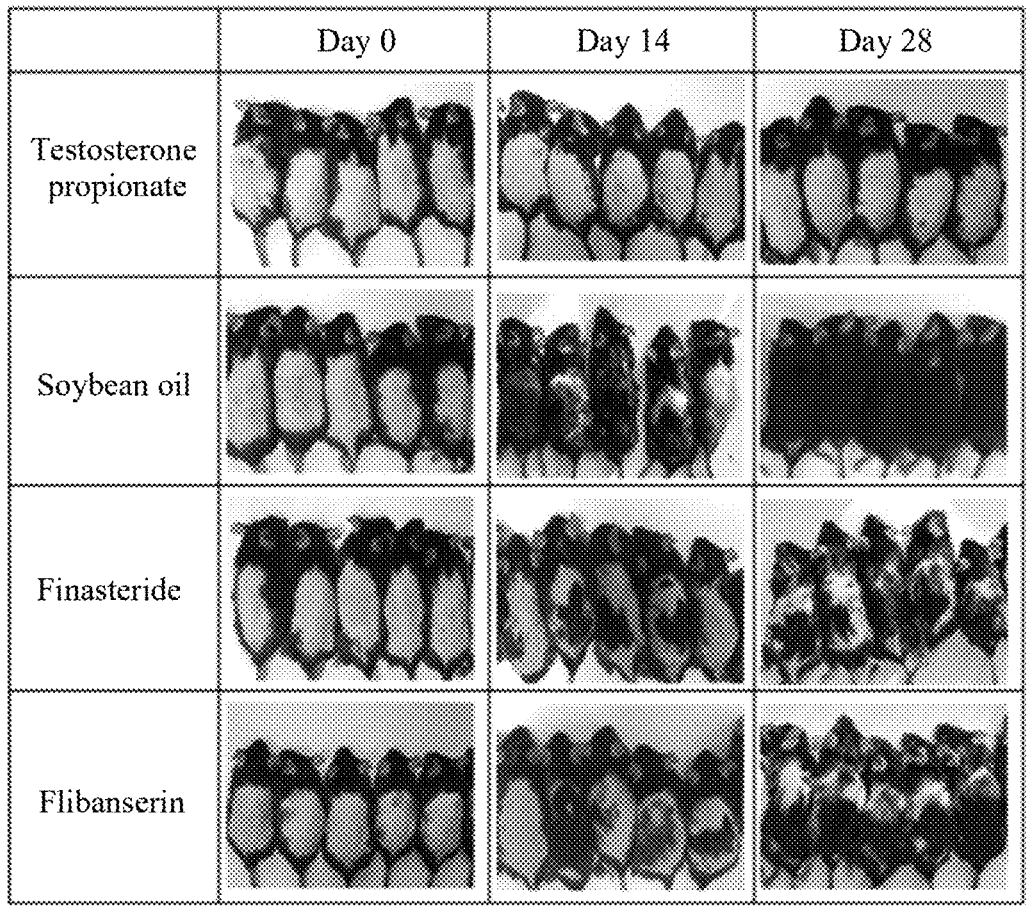
FIG. 8: Images of hair restoration in AGA model mice treated with flibanserin.

The results show that in the flibanserin administration group and finasteride administration group, the hairs of mice have restored to varying degrees compared with the model group, and the hair growth is similar to that in the control group and the complete blank group (FIG. 2). The effective rate of animal hair restoration is 85.7% in the flibanserin group and 71.4% in the finasteride group (FIG. 3). Compared with the model group, HE staining of tissue sections shows an increase in hair length, an increase in the ratio of anagen to telogen, an increase in the ratio of epidermal thickness to dermal thickness, an increase in the number of hair follicles per unit area, and an increase in the diameter of hair follicles in the flibanserin group (FIG. 4-FIG. 7). Therefore, the results show that flibanserin could reverse androgen-mediated androgenic alopecia damage, treat androgenic alopecia and restore hair growth (FIG. 8).

Table 3: Effective rate of drug in control group, finasteride group and flibanserin group

| Group | Control group | Finasteride | Flibanserin |
|---|---|---|---|
| Effective rate of drug | 100% | 71.4% | 85.7% |

Example 3

Mouse primary hair follicle dermal papilla cells were extracted according to enzymatic digestion and cultured for 10 days under culture conditions of L-DMEM (Nanjing KeyGen Biotech. Co. Ltd.) 88 ml+FBS (SenBeiJia Biological Technology Co., Ltd.) 10 ml+Glutamax (Invitrogen, 35050) 1 ml 1 ml. The primary cells grew to fill a T25 culture flask, and then passaged, wherein a part of the primary cells were used in flow cytometry experiments to identify cell surface markers, and the identification results were positive for CD56, CD133 and CD140a, and negative for CD73 and CD90, indicating that these cells were hair follicle dermal papilla cells. The cells were seeded into a 12-well plate, drug administration was performed to the blank group, the DHT group ($10^{-8}$ mol/L), the DHT ($10^{-8}$ mol/L)+finasteride group (5 μmol/L), the DHT ($10^{-8}$ mol/L)+high-dose flibanserin group (5 μmol/L), and the DHT ($10^{-8}$ mol/L)+low-dose flibanserin group (1 μmol/L), respectively, after 48 h, a nuclear protein and cytoplasmic protein separation experiment was performed using a nuclear protein and cytoplasmic protein separation kit from Beyotime according to instructions, and the separated nuclear protein and cytoplasmic protein were subjected to SDS-PAGE gel electrophoresis respectively.

Figure 9:
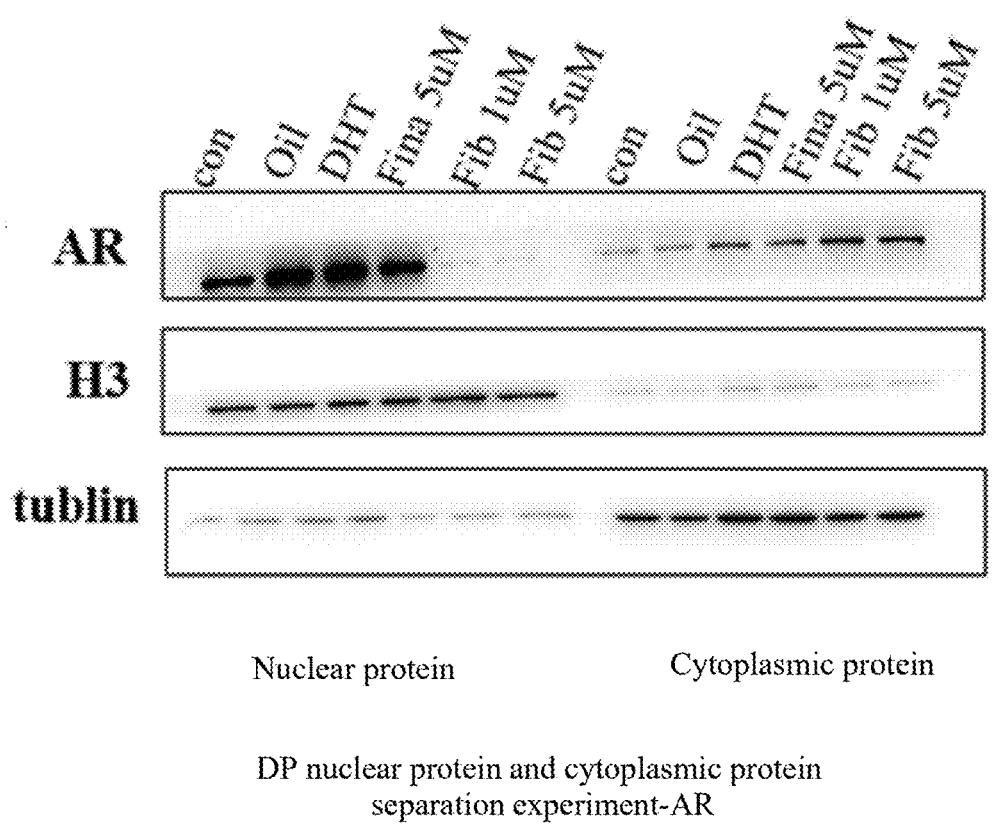
FIG. 9: Nuclear protein and cytoplasmic protein separation images that indicate that flibanserin inhibits the nuclear localization of the androgen receptor dimer.

The experimental results show that: with H3 as the internal reference for nuclear protein and B-Tublin as the internal reference for cytoplasmic protein, it can be seen from the images of proteins that only H3 protein is present in the nuclear protein group and only B-Tublin protein is present in the cytoplasmic protein group, indicating that the nuclear protein and cytoplasmic protein separation experiment is successful. The expression of the androgen receptor is up-regulated in the DHT group compared with the blank group. There is no significant difference between the level of the androgen receptor in the finasteride group and that in the DHT group and between the level of the androgen receptor in flibanserin groups with both doses and that in the DHT group, indicating that finasteride and flibanserin do not alter the total level of the androgen receptor; but the level of the androgen receptor in the nucleus is decreased and the level of the androgen receptor in the cytoplasm is increased in flibanserin groups with both doses compared with those in the finasteride group and the DHT group, indicating that flibanserin could inhibit the nuclear localization of the androgen receptor (FIG. 9).

The invention claimed is:

1. A method of treating androgenic alopecia in a subject, comprising administering an effective amount of flibanserin to the subject.

2. The method according to claim 1, wherein flibanserin can increase hair length, the ratio of anagen to telogen, the ratio of epidermal thickness to dermal thickness, the number of hair follicles per unit area, and the diameter of hair follicles.

3. The method according to claim 1, wherein flibanserin reverses androgen-mediated androgenic alopecia damage, treating androgenic alopecia, and restoring hair growth.

4. A method of treating androgenic alopecia in a subject by inhibiting an androgen receptor dimer and preventing it from entering the nucleus in the subject, comprising administering an effective amount of flibanserin to the subject.

* * * * *